(12) United States Patent
Lem et al.

(10) Patent No.: US 7,466,908 B1
(45) Date of Patent: Dec. 16, 2008

(54) SYSTEM FOR RAPID NUCLEIC ACID AMPLIFICATION AND DETECTION

(75) Inventors: Paul Lem, Toronto (CA); John Lem, Toronto (CA); Jamie Spiegelman, Toronto (CA)

(73) Assignee: Spartan Bioscience Inc., Ottawa, Ontario (CA)

( * ) Notice: Subject to any disclaimer, the term of this patent is extended or adjusted under 35 U.S.C. 154(b) by 64 days.

(21) Appl. No.: 11/578,440

(22) PCT Filed: Apr. 15, 2005

(86) PCT No.: PCT/CA2005/000576

§ 371 (c)(1),
(2), (4) Date: Oct. 13, 2006

(87) PCT Pub. No.: WO2005/100538

PCT Pub. Date: Oct. 27, 2005

Related U.S. Application Data

(60) Provisional application No. 60/563,061, filed on Apr. 16, 2004.

(51) Int. Cl.
*A61F 7/08* (2006.01)
(52) U.S. Cl. ............. 392/443; 219/428; 435/283.1
(58) Field of Classification Search ............... None
See application file for complete search history.

(56) References Cited

U.S. PATENT DOCUMENTS

| | | | |
|---|---|---|---|
| 4,581,333 A | 4/1986 | Kourilsky et al. | |
| 5,118,801 A | 6/1992 | Lizardi et al. | |
| 5,283,174 A | 2/1994 | Arnold, Jr. et al. | |
| 5,312,728 A | 5/1994 | Lizardi et al. | |
| 5,455,175 A | 10/1995 | Wittwer et al. | |
| 5,525,300 A | 6/1996 | Danssaert et al. | |
| 5,547,842 A | 8/1996 | Hogan et al. | |
| 5,639,604 A | 6/1997 | Arnold, Jr. et al. | |
| 5,656,207 A | 8/1997 | Woodhead et al. | |

(Continued)

FOREIGN PATENT DOCUMENTS

CA   2 450 343 A1   1/2003

(Continued)

OTHER PUBLICATIONS

Higuchi et al., *Biotechnology*, 10: 413-417 (1992).

(Continued)

*Primary Examiner*—Thor S Campbell
(74) *Attorney, Agent, or Firm*—Leydig, Voit & Mayer, Ltd.

(57) ABSTRACT

A temperature cycling system (10, 110) is provided for repeatedly heating and cooling a reaction mixture (16). The system (10, 110) includes a first heater (27) and a second heater (28) each movable between a first orientation in which the first or second heater (27, 28) affects the temperature of the reaction mixture (16) and a second orientation in which the first or second heater (27, 28) does not substantially affect the temperature of the reaction mixture (16). During temperature cycling, the second heater (28) is in the second orientation when the first heater (27) is in the first orientation, and the second heater (28) is in the first orientation when the first heater (27) is in the second orientation.

17 Claims, 7 Drawing Sheets

U.S. PATENT DOCUMENTS

| | | |
|---|---|---|
| 5,658,737 A | 8/1997 | Nelson et al. |
| 5,731,148 A | 3/1998 | Becker et al. |
| 5,779,981 A | 7/1998 | Danssaert et al. |
| 6,054,263 A | 4/2000 | Danssaert et al. |
| 6,174,670 B1 | 1/2001 | Wittwer et al. |
| 6,569,627 B2 | 5/2003 | Wittwer et al. |

FOREIGN PATENT DOCUMENTS

| | | |
|---|---|---|
| EP | 0 402 995 A2 | 12/1990 |
| EP | 0 747 706 A1 | 12/1996 |
| WO | 2004/029195 A2 | 4/2004 |

OTHER PUBLICATIONS

Higuchi et al., *Biotechnology*, 11: 1026-1030 (1993).
Holland et al., *Proc. Natl. Acad. Sci. USA*, 88: 7276-7280 (1991).
Saiki et al., *Science*, 230: 1350-1354 (1985).
Wittwer et al., *BioTechniques*, 10(1): 76-83 (1991).

| Lane # | Sample |
|---|---|
| 1 | 100 bp ladder |
| 2 | PCR amplification for 180-bp fragment of the mecA gene using the Thermal alternator (45 cycles in 13.5 mins) |
| 3 | PCR amplification for 180-bp fragment of the mecA gene using the GeneAmp® 2700 PCR machine (Applied Biosystems) |

| Lane # | Sample |
|---|---|
| 1 | 100 bp ladder |
| 2 | Multiplex PCR reaction for nuc (598 bp), mecA (392 bp) and 16S rRNA (312 bp) fragments using the Thermal alternator (45 cycles in 26 minutes) |
| 3 | Multiplex PCR reaction for nuc, mecA and 16S rRNA fragments using the GeneAmp® 2700 PCR machine (Applied Biosystems) (45 cycles in 80 minutes) |
| 4 | 100 bp ladder |

SYSTEM FOR RAPID NUCLEIC ACID AMPLIFICATION AND DETECTION

TECHNICAL FIELD

The present invention relates to a temperature cycling apparatus useful for performing nucleic acid amplification and detection. More specifically, the present invention relates to a thermal cycling apparatus for rapidly cycling the temperature of a sample through a predetermined temperature cycle.

BACKGROUND OF THE INVENTION

In numerous areas of industry, technology, and research there is a need to reliably and reproducibly subject relatively small reactions to thermal cycling. The need to subject a sample to repeated temperature cycles is particularly acute in biotechnology applications. In the biotechnology field, it is often desirable to repeatedly heat and cool small samples of materials over a short period of time. One such biological process that is regularly carried out is cyclic DNA amplification.

Cyclic DNA amplification, using a thermostable DNA polymerase, allows automated amplification of primer specific DNA, widely known as PCR, or the polymerase chain reaction. It is well accepted that automation of this process requires controlled and precise thermal cycling of reaction mixtures.

PCR is a technique involving multiple cycles that results in the geometric amplification of certain polynucleotide sequence each time a cycle is completed. The technique of PCR is well known to the person of average skill in the art of molecular biology and has been described in many books, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR has also been described in many U.S. patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, which are hereby incorporated by reference.

The PCR technique typically involves first denaturing a polynucleotide, followed by annealing at least a pair of primer oligonucleotides to the denatured polynucleotide, i.e., hybridizing the primer to the denatured polynucleotide template. After the annealing step, an amplicon extension step is completed using an enzyme with polymerase activity that catalyzes synthesis of a new polynucleotide strand that incorporates the primer oligonucleotide and uses the original denatured polynucleotide as a synthesis template. This series of steps (denaturation, primer annealing, and primer extension) constitutes a PCR cycle. As cycles are repeated, the amount of newly synthesized polynucleotide increases geometrically because the newly synthesized polynucleotides from an earlier cycle can serve as templates for synthesis in subsequent cycles. Primer oligonucleotides are typically selected in pairs that can anneal to opposite strands of a given double-stranded polynucleotide sequence so that the region between the two annealing sites is amplified.

One cycle of standard PCR is usually performed in 2 to 8 min requiring 1 to 4 hours for a 30-cycle amplification. The sample temperature response in most PCR instrumentation is very slow compared to the optimal durations required for denaturation, annealing, and extension. The physical (denaturation and annealing) and enzymatic (extension) reactions in PCR occur very quickly. Amplification times for PCR can be reduced from hours to less than 10 minutes. This can be accomplished by: (1) reducing the ramping time for the thermal cycler to change temperatures between the annealing, extension and denaturation steps; (2) reducing the run times for each of the 3 steps; and (3) reducing the temperature cycling profile from three different temperatures to two temperatures. This is accomplished by completing a two-step PCR cycling profile in which the annealing and extension steps are completed at the same temperatures.

Commercial programmable metal heat blocks have been used in the past to affect the temperature cycling of samples in microfuge tubes through the desired temperature versus time profile. Peltier heating and cooling are usually utilized in changing temperatures at a rate of approximately 0.5-4 degrees Celsius per second. However, the inability to quickly and accurately adjust the temperature of the heat blocks through a large temperature range over a short time period, has rendered the use of heat block type devices undesirable as a heat control system when carrying out the polymerase chain reaction in a rapid fashion.

Furthermore, devices using water baths with fluidic switching, (or mechanical transfer) have also been used as thermal cyclers for PCR. Although water baths have been used in cycling a PCR mixture through a desired temperature versus time profile, the high thermal mass and relatively low boiling point of water are significantly limiting factors in terms of rapid temperature time gradients. The 3-dimensional mechanical requirements of a water bath apparatus are also an impediment in terms of performance, accuracy and cost.

Devices using water baths are limited in their performance. This is because the water's thermal mass significantly restricts the maximum temperature versus time gradient which can be achieved thereby. Also, the water bath apparatus has been found to be very cumbersome due to the size and number of water carrying hoses and external temperature controlling devices for the water. Further, the need for excessive periodic maintenance and inspection of the water fittings for the purpose of detecting leaks in a water bath apparatus is tedious and time consuming. Finally, it is difficult with the water bath apparatus to control the temperature in the sample tubes with the desired accuracy.

A wide variety of instrumentation has been developed for carrying out nucleic acid amplifications, particularly PCR, e.g. Johnson et al, U.S. Pat. No. 5,038,852 (computer-controlled thermal cycler); Wittwer et al, Nucleic Acids Research, 17: 4353-4357 (1989)(capillary tube PCR); Hallsby, U.S. Pat. No. 5,187,084 (air-based temperature control); Garner et al, Biotechniques, 14: 112-115 (1993)(high-throughput PCR in 864-well plates); Wilding et al, International application No. PCT/US93/04039 (PCR in micromachined structures); Schnipelsky et al, European patent application No. 0 381 501 A2 (disposable, single use PCR device), and the like. Important design goals fundamental to PCR instrument development have included fine temperature control, minimization of sample-to-sample variability in multi-sample thermal cycling, automation of pre- and post-PCR processing steps, high speed cycling, minimization of sample volumes, real-time measurement of amplification products, minimization of cross-contamination, or sample carryover, and the like.

Another prior art system is represented by a temperature cycler in which multiple temperature controlled blocks with vertical reaction vessel wells are maintained at different desired temperatures (U.S. Pat. Nos. 5,525,300, 5,779,981 and 6,054,263). A robotic arm is utilized by move reaction mixtures from block to block. The reaction vessels are lifted vertically from out of the heat block, transported to another heating block, and placed vertically down into said heating block. However, this system requires precision movement, pressurized thermal contact and expensive microprocessor controlled robotics. This robotic movement system also impedes a real-time fluorescent detection system of the nucleic acid amplification product during and after temperature cycling has completed.

Rapid cycling has been described before (e.g. U.S. Pat. No. 6,174,670, and U.S. Pat. No. 5,455,175). According to this prior art, rapid cycling techniques are made possible by the rapid temperature response and temperature homogeneity possible for samples in high surface area-to-volume sample containers such as capillary tubes. For further information, see also: C. T. Wittwer, G. B. Reed, and K. M. Ririe, Rapid cycle DNA amplification, in K. B. Mullis, F. Ferre, and R. A. Gibbs, The polymerase chain reaction, Birkhauser, Boston, 174-181, (1994). According to this prior art, improved temperature homogeneity allows the time and temperature requirements of PCR to be better defined and understood, while improved temperature homogeneity also increases the precision of any analytical technique used to monitor PCR during amplification.

The design of instruments that permit PCR to be carried out in closed reaction chambers and monitored in real time is highly desirable. Closed reaction chambers are desirable for preventing cross-contamination, e.g. Higuchi et al, Biotechnology, 10: 413-417 (1992) and 11: 1026-1030 (1993); and Holland et al, Proc. Natl. Acad. Sci., 88: 7276-7280 (1991). Clearly, the successful realization of such a design goal would be especially desirable in the analysis of diagnostic samples, where a high frequency of false positives and false negatives would severely reduce the value of the PCR-based procedure. Real-time monitoring allows the coupling of amplification and detection, thus decreasing contamination risks and labour time. As well, real-time monitoring of a PCR permits far more accurate measurement of starting target DNA concentrations in multiple-target amplifications, as the relative values of close concentrations can be resolved by taking into account the history of the relative concentration values during the PCR. Real-time monitoring also permits the efficiency of the PCR to be evaluated, which can indicate whether PCR inhibitors are present in a sample.

Holland et al (cited above) and others have proposed fluorescence-based approaches to provide real-time measurements of amplification products during a PCR. Such approaches have either employed intercalating dyes (such as ethidium bromide) to indicate the amount of double stranded DNA present, others have employed probes containing fluorescent-quencher pairs (the so-called "Taq-Man™" approach) that are cleaved during amplification to release a fluorescent product whose concentration is proportional to the amount of double stranded DNA present. Other fluorescent probe technologies have also been used in real-time PCR, including Fluorescent Resonance Energy Transfer (FRET) probes (U.S. Pat. Nos. 6,174,670 and 6,569,627), linear probes in which one probe stimulates and adjacent probes to fluoresce, and molecular beacons in which a hairpin loop is formed within the probe to quench the florescence when the probe is not hybridized to the target nucleic acid.

Fluorimetry is a sensitive and versatile technique with many applications in molecular biology. Ethidium bromide has been used for many years to visualize the size distribution of nucleic acids separated by gel electrophoresis. The gel is usually trans-illuminated with ultraviolet light with a peak wavelength of 340 nm and the resultant fluorescence of double stranded nucleic acid observed at a peak wavelength of 610 nm. Specifically, ethidium bromide is commonly used to analyze the products of PCR after amplification is completed. Furthermore, EP 0 640 828 A1 to Higuchi & Watson, hereby incorporated by reference, discloses using ethidium bromide during amplification to monitor the amount of double stranded DNA by measuring the fluorescence each cycle. The fluorescence intensity was noted to rise and fall inversely with temperature. The greatest fluorescence occurred at the annealing/extension temperature (50° C.). The least fluorescence occurred at the denaturation temperature (94° C.). Maximal fluorescence acquired after each cycle correlated to the amount of nucleic acid amplification product.

The Higuchi & Watson application, however, does mention using other fluorophores, including dual-labeled probe systems that generate fluorescence when hydrolyzed by the 5'-exonuclease activity of certain DNA polymerases, as disclosed in U.S. Pat. No. 5,210,015 to Gelfand et al. The fluorescence observed from these probes primarily depends on hydrolysis of the probe between its two fluorophores. The amount of PCR product is estimated by acquiring fluorescence once each cycle.

The specific hybridization of nucleic acid to a complementary strand for identification has been exploited in many different formats. For example, after restriction enzyme digestion, genomic DNA can be size fractionated and hybridized to probes by Southern blotting. As another example, single base mutations can be detected by "dot blots" with allele-specific oligonucleotides. Usually, hybridization is performed for minutes to hours at a single temperature to achieve the necessary discrimination. Alternately, the extent of hybridization can be dynamically monitored while the temperature is changing by using fluorescence techniques. For example, fluorescence melting curves have been used to monitor hybridization. L. E. Morrison & L. M. Stols, Sensitive fluorescence-based thermodynamic and kinetic measurements of DNA hybridization in solution, 32 Biochemistry 3095-3104, 1993). The temperature scan rates are usually 10° C./hour or less, partly because of the high thermal mass of the fluorimeter cuvette. The temperature scan, or melting analysis, was applied to real-time PCR by Wittwer C T et al. in U.S. Pat. No. 6,174,670.

The prior art in thermal cyclers, as explained above, carries out temperature cycling slowly or uses costly apparatus and unconventional reaction vessels. In the laboratory, there remains a need for a rapid, robust and cost-effective thermal cycler, especially one that can be easily coupled with a fluorescence detection system. Thus, it would be a great advance in the art to provide a system that is able to complete the amplification of nucleic acids with minimal ramp time and a robust design. It would also be beneficial for such a system to permit real-time analysis of the reaction without manipulation of the sample.

SUMMARY OF THE INVENTION

In view of the above described state of the art, the present invention seeks to realize the following objects and advantages.

It is an object of the present invention to provide an apparatus for accurately controlling the temperature of biological samples.

It is a further object of the present invention to provide a thermal cycling apparatus for quickly and accurately varying the temperature of biological samples according to a predetermined temperature versus time profile.

It is also an object of the present invention to provide a thermal cycling apparatus that can effectively subject samples to a large temperature gradient over a very short period of time.

It is a further object of the present invention to provide an apparatus that can subject a biological sample to rapid thermal cycling by rapidly alternating the sample between two heating blocks, which may be in opposing relation to one another.

It is another object of the present invention to provide a thermal cycling apparatus that will heat samples located in a fluid chamber placed in an engraved groove in the side of the heating blocks.

In yet another object of the invention, the two heating blocks are positioned in ambient air, and a portion of the reaction vessel while in the heating block is exposed to air without compromising a thermal gradient within the reaction vessel.

It is also an object of the invention to provide a real-time nucleic amplification product detection mechanism between the two heating blocks by means of fluorescence monitoring of said product labeled with a fluorescent dye.

The apparatus of the present invention includes a controlling means for operating the apparatus through the desired time versus temperature profile. The present invention is particularly well suited for carrying out automated and rapid polymerase chain reactions.

The controller of the present invention allows the chamber, and subsequently the samples located in the sample compartment therein, to pass through a predetermined temperature cycle corresponding to the denaturation and annealing/elongation steps in the polymerase chain reaction. In use, the apparatus of the present invention allows rapid optimization of denaturation, and annealing/elongation steps in terms of time and temperature, and shortened or minimal time periods (ramp times) between the temperatures at each step.

The present invention particularly decreases the total time required for completion of polymerase chain reaction cycling over prior art thermal cycling devices by having high reaction vessel liquid ramp time (>10° C./sec), by decreasing the number of steps per cycle from three to two (the annealing and extension steps are done at one temperature), and by decreasing the amount of time for each step of each cycle without compromising amplification efficiency.

The invention relates to a system for carrying out rapid nucleic acid amplification using PCR, which can be couple with real-time fluorescence-based measurements of nucleic acid amplification products. In one preferred embodiment of the invention, an excitation beam is focused into a reaction mixture containing a nucleic acid intercalating dye or hybridization probe which fluoresces proportionally to the amount of nucleic acid amplification product. It is understood that the proportionality of the fluorescent intensities is for a constant set of parameters such as temperature, pH, salt concentration, and the like, that independently influence the fluorescent emissions of organic dyes.

Preferably, the excitation beam is focused into the reaction mixture through a lens through a portion of a wall of a closed reaction chamber containing the reaction mixture.

In the most preferred embodiment, the reaction chamber is a reaction vessel with a closed end, referred to herein as the bottom of the vessel, and an open end, referred to herein as the top of the vessel, which can be closed with a cap such that a leak-proof seal is formed. In other words, once a reaction mixture is placed in the vessel and the cap is attached a closed reaction chamber is formed. In this most preferred embodiment, (1) the reaction mixture fills a portion of the reaction vessel, generally at the bottom of the vessel, such that a void is left between the cap of the vessel and a top surface of the reaction mixture, and (2) the reaction is completed in the apparatus described above and (3) the lens, without contacting the side of the vessel, allows the excitation beam through the vessel wall into the reaction mixture through its side surface and (4) the resulting fluorescence generated by the fluorescent indicator is collected by a photosensor, such as a photodiode, at various time points.

As discussed more fully below, an excitation beam generated by a single light source, e.g. a Light Emitting Diode (LED), is placed on one side of the vessel. The wavelength of the excitation beam is restricted by appropriately selecting a colored type of LED as well as using a color filter by which LED light travels through. Likewise, a different color filter located on the opposite side of the vessel restricts the resultant emission fluorescence wavelength. A photodiode sensor collects the filtered emission light and the amplitude of the emission is examined and compared by an analysis system.

Preferably, the system is employed with the PCR amplification of nucleic acids.

The system of the invention permits accurate real-time monitoring of nucleic amplification reactions by providing apparatus and fluorescent reagents for generating a stable fluorescent signal proportional to the amount of amplification product and independent of variations in the volume of reaction mixture. The availability of data showing the progress of amplification reactions leads to rapid assessment of the efficiency of the amplification reactions, and opens the possibility of reduced reagent usage and feedback reaction control.

These and other objects and advantages of the invention will become more fully apparent from the description and claims which follow, or may be learned by the practice of the invention.

BRIEF DESCRIPTION OF THE DRAWINGS

The invention will be better understood by reference to the appended figures of which.

DETAILED DESCRIPTION OF THE INVENTION

Figure 1:
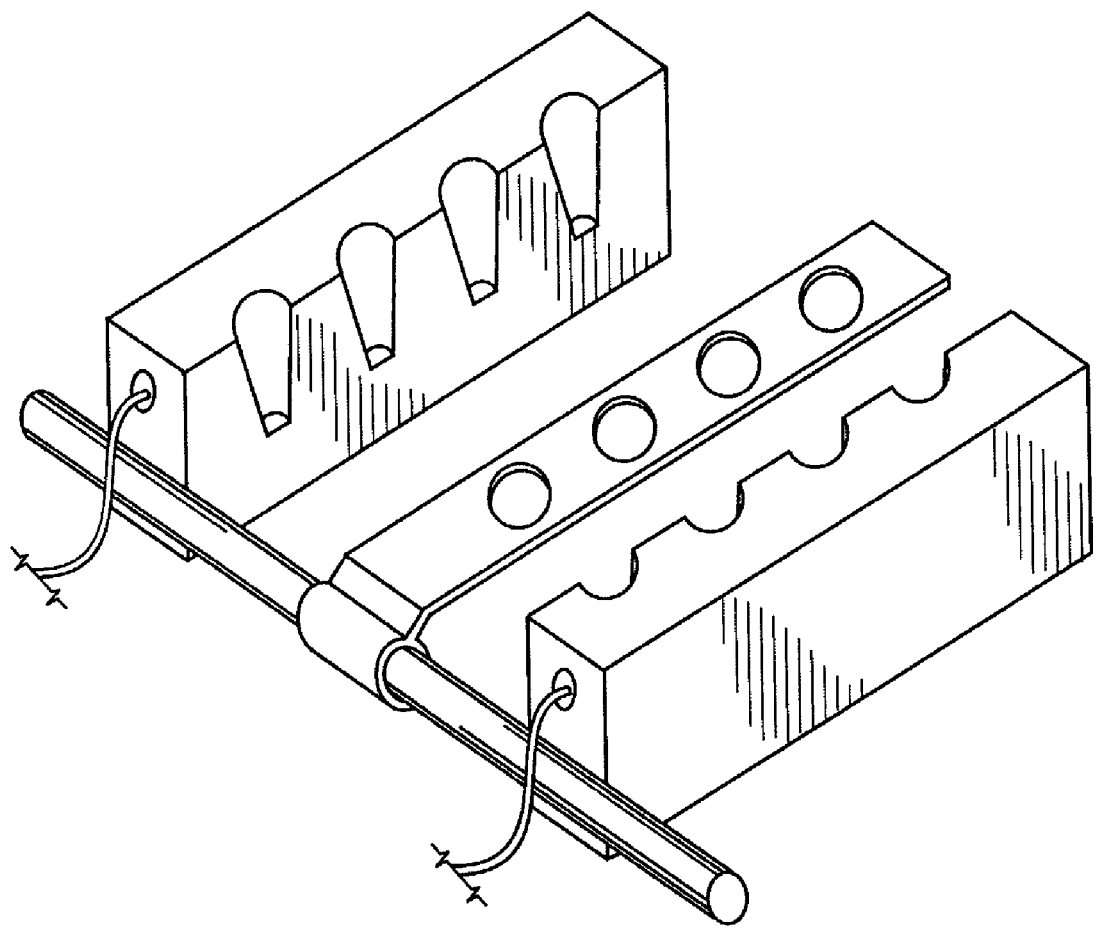
FIG. 1: is a perspective view of a thermal alternator device according to one embodiment of the invention, which is adapted for thermal cycling of biological samples and adapted especially for use in cyclic DNA amplification, according to the concepts of the present invention. The device incorporates the two-block/one-dimension of the invention.

Before the present system for rapid cycling, amplification and detection are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

In describing and claiming the present invention, the following terminology will be used in accordance with the definitions set out below.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

"Amplification" of DNA as used herein denotes the use of polymerase chain reaction (PCR) to increase the concentration of a particular DNA sequence within a mixture of DNA sequences.

An "amplicon" is a product of the amplification of a target genetic sequence.

A "PCR reaction mixture" as used herein denotes a mixture adaptable for simultaneously amplifying multiple genetic targets under suitable conditions for PCR.

A "genetic target" as used herein denotes a genetic sequence capable of amplification by polymerase chain reaction (PCR). A genetic target in accordance with the present invention includes any DNA sequence, including bacterial, viral, fungal, human, plant, and animal DNA, for example.

As used herein, "continuous monitoring" and similar terms refer to monitoring multiple times during a cycle of PCR, preferably during temperature transitions, and more preferably obtaining at least one data point in each temperature transition.

As used herein, "fluorescence detection" and similar terms refer to labeling nucleic acids with a fluorescence indicator. The fluorescence indicator can be a nucleic acid intercalating dye such as Ethidium Bromide, Thiazole orange, Pico™ Green or SyBr™ Green. As well, labeled hybridization probes using FRET, Taq-Man™ or other chemistries such as molecular beacons can also be used as fluorescence detection tools.

As used herein, "effective amount" means an amount sufficient to produce a selected effect. For example, an effective amount of PCR primers is an amount sufficient to amplify a segment of nucleic acid by PCR provided that a DNA polymerase, buffer, template, and other conditions, including temperature conditions, known in the art to be necessary for practicing PCR are also provided.

The term "probe", as used herein, refers to a nucleic acid oligomer that hybridizes specifically to a target sequence in a nucleic acid, which, in the context of the present invention, is an amplicon, under standard conditions that promote hybridization. This allows detection of the amplicon. Detection may either be direct (i.e., resulting from a probe hybridizing directly to the amplicon sequence) or indirect (i.e., resulting from a probe hybridizing to an intermediate molecular structure that links the probe to the target amplicon). A probe's "target" generally refers to a sequence within (i.e., a subset of) an amplified nucleic acid sequence which hybridizes specifically to at least a portion of a probe oligomer using standard hydrogen bonding (i.e., base pairing). A probe may comprise target-specific sequences and other sequences that contribute to three-dimensional conformation of the probe (e.g., as described in Lizardi et al., U.S. Pat. Nos. 5,118,801 and 5,312,728).

By "sufficiently complementary" is meant a contiguous nucleic acid base sequence that is capable of hybridizing to another base sequence by hydrogen bonding between a series of complementary bases. By definition, this allows stable hybridization of a probe oligomer to a target sequence in the amplicon even though it is not completely complementary to the probe's target-specific sequence. Complementary base sequences may be complementary at each position in the base sequence of an oligomer using standard base pairing or may contain one or more residues that are not complementary using standard hydrogen bonding (including a basic "nucleotides"), but in which the entire complementary base sequence is capable of specifically hybridizing with another base sequence in appropriate hybridization conditions. Contiguous bases are preferably at least about 80%, more preferably at least about 90%, and most preferably greater than 95% complementary to a sequence to which an oligomer is intended to specifically hybridize. To those skilled in the art, appropriate hybridization conditions are well known, can be predicted based on base composition, or can be determined empirically by using routine testing (e.g., see Sambrook et al., Molecular Cloning, A Laboratory Manual, $2^{nd}$ ed. (Cold Spring Harbor Laboratory Press, Cold Spring Harbor, N.Y., 1989) at §1.90-1.91, 7.37-7.57, 9.47-9.51 and 11.47-11.57 particularly at §9.50-9.51, 11.12-11.13, 11.45-11.47 and 11.55-11.57).

The terms "label" and "detectable label", as used herein, refer to a molecular moiety or compound that can be detected or can lead to a detectable response. A label is joined, directly or indirectly, to a nucleic acid probe. Direct labeling can occur through bonds or interactions that link the label to the probe, including covalent bonds or non-covalent interactions (e.g., hydrogen bonding, hydrophobic and ionic interactions) or through formation of chelates or co-ordination complexes. Indirect labeling can occur through use of a bridging moiety or "linker," such as an antibody or additional oligonucleotide (s), which is either directly or indirectly labeled, and which can amplify a detectable signal. A label can be any known detectable moiety, such as, for example, a radionuclide, ligand (e.g., biotin, avidin), enzyme or enzyme substrate, reactive group, chromophore, such as a dye or particle that imparts a detectable color (e.g., latex or metal particles), luminescent compound (e.g., bioluminescent, phosphorescent or chemiluminescent labels) and fluorescent compound.

PCR techniques applicable to the present invention include inter alia those described in "PCR Primer: A Laboratory Manual", Dieffenback, C. W. and Dveksler, G. S., eds., Cold Spring Harbor Laboratory Press (1995); "Enzymatic amplification of beta-globin genomic sequences and restriction site analysis for diagnosis of sickle cell anemia", Saiki R K, Scharf S, Faloona F, Mullis K B, Horn G T, Erlich H A, Arnheim N, Science (1985) December 20; 230(4732):1350-4.

The PCR of the present invention is performed using a modified 2-step cycling profile as compared to standard PCR, namely successive cycles of denaturation of double stranded target nucleic acid and annealing/extension of the primers to produce a large number of copies of segments of the target DNA. Each cycle is a thermal cycle in which the reaction temperature is raised to denature the double stranded DNA and lowered to allow annealing and extension.

In one embodiment of the present invention, the PCR makes use of successive two-step cycles in which the temperature is raised to a first temperature for denaturation of the double stranded DNA and lowered to a second temperature to allow annealing and extension of the primers.

Following amplification of a nucleic acid using the system described herein, the amplicons may be detected using any method known in the art, including, without limitation: gel electrophoresis in agarose or acrylamide gels; real-time detection; non-isotopic calorimetric detection; chemiluminescent, and fluorescent detection. Detection may be quantitative or qualitative depending on the techniques used. Generally, in the case of quantitative detection, an internal standard is incorporated in the multiplex PCR by including a known amount of standard DNA target and an associated primer pair in the reaction. The quantity of amplicons produced from the internal standard target is then correlated to the quantity of the amplicons produced the target DNA in the sample in order to determine the amount of target DNA in the initial sample.

The detection of amplicons indicates the presence of target nucleic acid in the sample. When gel electrophoresis is used, amplicons are confirmed by their size, as predicted by the location in the respective target sequences corresponding to the amplification primers used in the PCR. A specific embodiment of the present invention provides a method in which the amplicons are detected using agarose gel electrophoresis with staining, for example, using ethidium bromide or SyBr™ Green.

Alternatively, the amplicons are detected using a hybridization assay. In this case, nucleic acid probes that are complementary to regions of the amplified DNA are hybridized to the denatured amplicons. The probes are labeled to allow visualization, and, optionally, quantification of the amplicons hybridized.

Preferably, the label on a labeled probe is detectable in a homogeneous assay system, i.e., where, in a mixture, bound labeled probe exhibits a detectable change, such as stability or differential degradation, compared to unbound labeled probe, without physically removing hybridized from non-hybridized forms of the label or labeled probe. A "homogeneous detectable label" refers to a label whose presence can be detected in a homogeneous fashion, for example, as previously described in detail in Arnold et al., U.S. Pat. No. 5,283,174; Woodhead et al., U.S. Pat. No. 5,656,207; and Nelson et al., U.S. Pat. No. 5,658,737. Examples of labels that can be used in a homogenous hybridization assay include, but are not limited to, chemiluminescent compounds (e.g., see U.S. Pat. Nos. 5,656,207, 5,658,737 and 5,639,604), such as acridinium ester ("AE") compounds, including standard AE or derivatives thereof. Synthesis and methods of attaching labels to nucleic acids and detecting labels are well known in the art (e.g., see Sambrook et al., Molecular Cloning, A Laboratory Manual, 2nd ed. (Cold Spring Harbor Laboratory Press, Cold Spring Harbor, N.Y., 1989), Chapter 10; U.S. Pat. Nos. 5,658,737, 5,656,207, 5,547,842, 5,283,174, 4,581,333 and European Patent Application No. 0 747 706).

In accordance with another embodiment of the present invention, where the amplicons are detected using an assay without prior separation of the amplicons, they are detected using different detectable molecules to allow the amplicons from the different primer pairs to be distinguishable. For example, probes used to hybridize to the various amplicons can be labeled with labels that are detectable at different wavelengths.

In accordance with another embodiment of the present invention, the amplicon production is monitored in real-time using procedures known in the art (e.g. see U.S. Pat. No. 6,569,627) and using the detection apparatus of the present invention.

It has now been found that, rapid thermal cycling can occur using a temperature spectrum and cycling between exact temperatures is not required for successful PCR. In the past PCR has been understood to be a combination of three sequential reactions (i.e. denaturation, annealing, extension) occurring at three different temperatures for three time periods. The present invention makes use of the fact that each of the reactions within PCR can occur over a range of temperatures and these temperatures overlap. Denaturation and annealing each occur so rapidly that no holding time at a particular temperature is necessary for these reactions to occur. Extension occurs over a range of temperatures at varying rates and can occur between the denaturation temperature and annealing temperature. As a result, the method of the present invention makes use of a single temperature for both the annealing and extension portions of PCR.

Some advantages of the techniques contained herein are based on rapid cycling, with its advantages in speed and specificity.

Technical Description of the Rapid Thermal Alternator

The present invention provides a thermal cycler device for performing reactions, such as PCR, using at least two different temperature blocks, each maintained at a different temperature. Each temperature block is configured to receive one or more reaction vessels such that only a portion of the outer surface of the one or more reaction vessels is in direct contact with the temperature block. As a result of this configuration, the reaction vessel or vessels can be moved from one temperature block to the other using a one-dimensional movement of either the reaction vessel(s) or the temperature blocks, or a combination thereof.

In the past, thermal cyclers having more than one temperature block have required that the reaction vessels be lifted from a receptacle in one temperature block, moved over and lowered into a receptacle in the second temperature block. In the past this design has been used for performing PCR because it was previously believed that the most effective way to achieve precise temperature control of the reaction mixture was to maximize the surface area of the reaction vessel in direct contact with the temperature source. It has now been found that maximizing the amount of reaction vessel surface in direct contact with the temperature block is not required for efficient PCR. In fact, only a portion of the outer surface of the reaction vessel surface needs to be in direct contact with the temperature block. It is only necessary that the amount of outer surface in direct contact with the temperature block be sufficiently large to allow the reaction mixture within the vessel to reach thermal equilibrium.

The amount of surface area contact between the heating block and the reaction vessel will influences the rate at which thermal equilibrium of the reaction mixture is reached. The higher the amount of surface area contact, the faster the speed at which thermal equilibrium is reached and vice versa. Faster thermal equilibration can also be influenced by other factors, including, but not limited to, the thickness of the reaction vessel wall, the thermal conductivity of the material of the reaction vessel, the thermal conductivity of the heating block, the shape of the reaction vessel, the shape of the reaction vessel receiving groove within each temperature block and the volume of the reaction mixture. For example, a reaction vessel having a thinner wall will allow a reaction mixture to reach thermal equilibrium faster than a reaction vessel made of the same material but having a thicker wall. Similarly, a small reaction volume will reach thermal equilibrium faster than a large reaction volume.

The above factors can be altered depending on the intended application of the device of the present invention. Similarly, the amount of direct surface area contact between the outer surface of the reaction vessel and the temperature contact can be varied depending on the intended application. For example, if faster thermal equilibration is required then a larger direct surface area contact is required than if a slow thermal equilibration is satisfactory.

In accordance with a specific embodiment of the present invention, a standard PCR tube is used as the reaction vessel and at least about 40% of the outer surface of the reaction vessel (wherein the outer surface does not include the surface of any lid present on the reaction vessel) must be in direct contact with the temperature block.

In accordance with one embodiment of the present invention, the system contains two temperature blocks. In this embodiment, transfer of the reaction vessel or vessels between the two reaction blocks is achieved either by one-dimensional movement of the vessel or vessels or by one-dimensional movement of the temperature blocks. In a specific embodiment of the present invention, the reaction vessel or vessels are held by holding means attached to a horizontal transfer means, such as a robotic arm, that transfers the vessels or vessels via a substantially horizontal movement between the two temperature blocks.

In an alternative embodiment, the system of the present invention comprises three or more temperature blocks. As in the two-block system, the reaction vessel(s) is moved, or the blocks are moved, such that the reaction vessel is in direct contact with only one temperature block at a time.

Figure 2A:
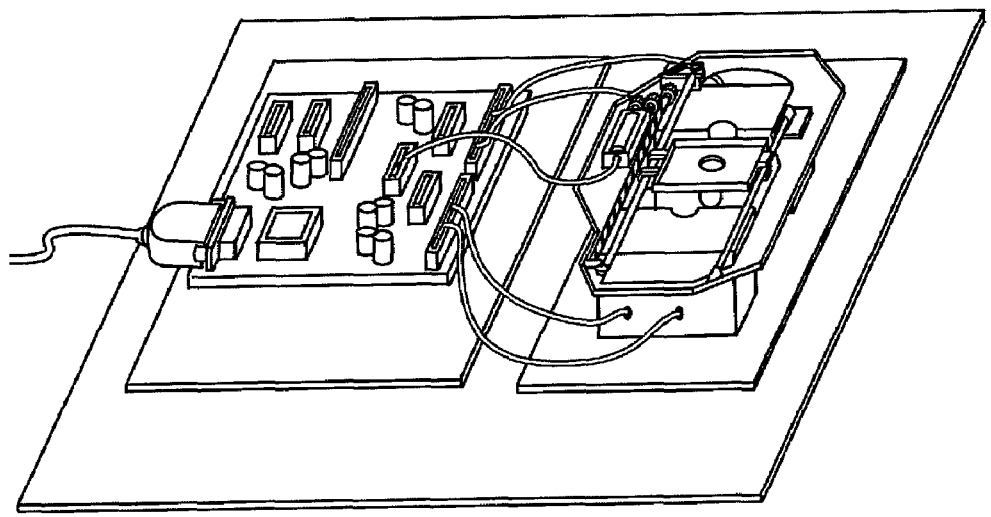
FIG. 2: (A) is a photographic perspective view of a thermal alternator according to one embodiment of the invention, incorporating the two-block/one-dimension of the invention and the surrounding microcontrollers (no fluorescence detection system). (B) is a photographic perspective view of a thermal alternator according to one embodiment of the invention, incorporating the two-block/one-dimension of the invention and the surrounding microcontrollers (fluorescence detection is integrated).
Figure 2B:
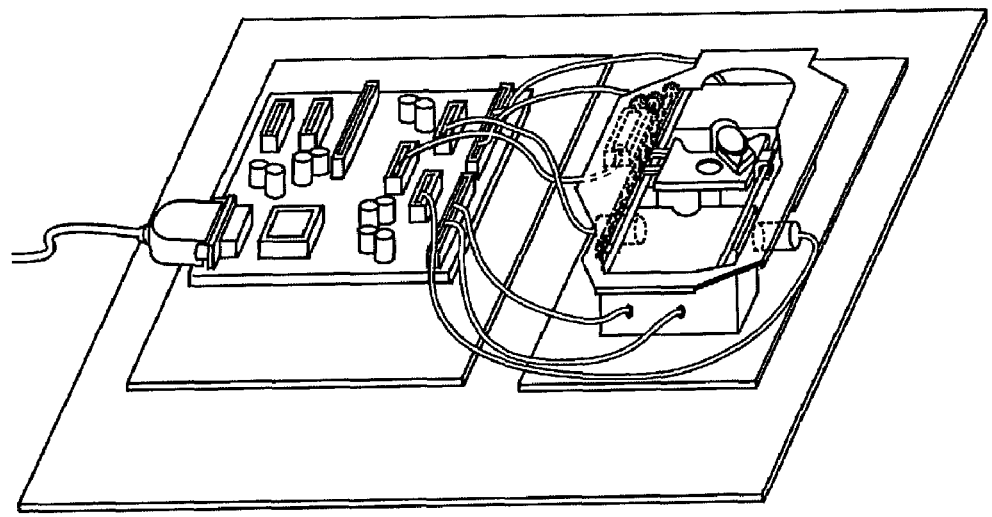

FIGS. 1 and 2 depict a thermal cycling device according to a specific embodiment of the present invention. As shown in FIGS. 1 and 2, the device includes two metal blocks, constructed out of aluminum or copper. Each encloses a heating element, such as a resistive heating element. Each metal block includes at least one receiving means for receiving the reaction vessel. Above the two metal blocks is a horizontal translation means, for example, a mechanical arm as shown in FIGS. 1 and 2, for moving the reaction vessel between the two heating blocks. The device also includes a controller (e.g. a microcontroller) that can be programmed, for example, by means of input keys, to cause the reaction vessel to be cycled through a series of temperatures over a predetermined period of time. The thermal cycling of the reaction vessel can be used to carry out numerous procedures and is particularly suited for nucleic acid amplification, as outlined herein. It should be understood, however, that the thermal cycler device of the present invention can be used for performing any reaction that requires successive cycling between two temperatures.

In accordance with the embodiment of the present invention depicted in FIGS. 1 and 2, the metal heating block is shaped generally in a rectangular box configuration and is attached to a mounting plate. A thin insulating material, such as plastic, is attached to the bottom of each heating block so as to minimize heat transfer from the block to the mounting plate. The heating blocks are mounted to the plate by thermally insulating glue or by metal braces to secure them.

Attached to each metal block is a resistive heating element which provides joule heat transfer energy to heat the block. The resistive heating element is preferably enclosed inside a portion of the heating block and surrounded by thermally conductive paste which provides better heat transfer contact between the heating element and metal block. Alternatively, the resistive heating element may be completely surrounded by the metal block by being cast at the time of molding. The resistive heating element is connected via wires to a circuit and controller which will be described further below.

A heat sensor, for example a thermistor, is attached to the outer edge of each metal heating block. To facilitate accurate surface temperature reading, the heat sensor may be placed just under the surface of the metal block, enclosed by thermal transfer compound. The heat sensor is connected via wires to a circuit and controller which will be described further below.

As shown in FIG. 1, each heating block has a vessel-shaped slot cut into the upper side facing each other that acts as receiving means for the reaction vessel. Each slot may be coated with a low-friction, high heat transfer film such as Teflon, to ensure uniform and rapid heating of the vessel as it is moved into the slot. The slot is shaped as to completely contact the reaction vessel on all sides except the facing side opposite the other metal heating block.

The reaction vessel can be a standard conical PCR reaction tube (e.g. 200 µl volume) or alternatively can be a rectangular cuvette. The reaction vessel is preferably designed with a thin-walled transparent material that facilitates heat transfer between the heating block and the reaction mixture within the reaction vessel when a portion of the outer surface of the vessel is in direct contact with the heating block. Preferably the vessel has a rim about the periphery of its top, which provides a seating surface for contact with the holding means attached to the mechanical arm. A flat cap that sits partially inside the top of the vessel seals the top of the tube, providing an air tight seal to prevent evaporation. The walls of the vessel are formed to be vertically rigid up to a temperature of about 100° C. to ensure a tight seal with the vessel slot of the metal heating block during heating. The vessel is formed from a transparent material, preferably a plastic such as a polypropylene derivative or glass. Preferably, the vessel has high transmittance of visible light, low vessel wall gas permeability and sterile inner surface.

As shown in FIG. 2, the arm mechanism is designed as to transport the reaction vessel horizontally between the vessel slots of the metal heating blocks. To move the arm mechanism, a DC motor with a threaded shaft is attached to a gear or set of gears. A lubricating substance may be placed between the gears to increase smooth gear movement. The gearing of the DC motor reduces the effective rotations per minute (RPM) of the motor and provides frictional force to stop and start the arm mechanism. As shown in FIG. 2, the platform which houses the reaction vessel is mounted parallel to two circular metal rods. On each end of the platform is a semicircular "U" shaped attachment which allows the platform to move freely, with minimal friction, between the two parallel circular metal rods. A lubricating substance can be placed between the "U" shaped attachments and metal rods to reduce frictional force. On one end of the platform, a straight gear with teeth is attached to the DC motor gear set. As the motor rotates and drives the gear set, the platform, by method of frictional movement between gears, drives the platform along the two parallel circular metal rods. The motor is connected via wires to a circuit and controller which will be described further below.

As shown in FIG. 2, the purpose of the platform is to hold in place the reaction vessel. Located near the middle of the platform is an opening through which the reaction vessel is placed. The rim of the vessel sits directly around the opening to hold the vessel in place. Optionally, a flat metal lid is attached and covers the area of the platform which houses the top of the vessel. The metal lid is attached to a hinge and has a clamping mechanism to provide pressure on the top of vessel. The pressure of the metal lid on the top of the vessel ensures the vessel is held securely in place and will remain perpendicular to the horizontal orientation of the platform. The metal lid may also have a resistive heating element mounted to its service. The purpose of the resistive heating element is to transfer heat from the metal lid to the top of the vessel. If the heated metal lid is set to a temperature above the maximum temperature of the vessel, it will minimize condensation of the reaction solvent at the top of the cap of the vessel, which would increase reactant concentration and potentially adversely affect reaction efficiency.

The heated metal lid is connected via wires to a circuit and controller which will be described further below. Alternatively, if a heated metal lid is not included, the reaction can be overlaid with a mineral oil, or a similar substance, which would also minimize or eliminate condensation of the reaction solvent on the lid of the vessel. A substance, such as mineral oil, with a boiling point much greater than the reaction solvent reduces evaporation of the reaction solvent.

As shown in FIG. 2, the entirety of the arm mechanism is mounted so that it does not come in contact with the metal heating blocks or impede the movement of the vessel. One such method is by securing the arm mechanism with posts attached to the base and arm mechanism.

The circuit board is electrically attached by means of wires to the resistive heating elements attached to each metal block, the temperature sensors attached to each metal block, the motor driving the arm movement, and the microcontroller. The circuit board consists of:

Circuit 1—a current or voltage regulator circuit for the resistive heating elements Circuit 2—a temperature sensor circuit for the metal block temperature sensors Circuit 3—a motor driver circuit for the arm movement motor The current or voltage regular circuit, Circuit 1, regulates the current and voltage passed to the resistive heating elements. Circuit 1 can be any well known current and voltage regulator, such as a MOSFET circuit driver or relay driver. The current and voltage passed to the resistive heating elements is regulated by the microcontroller.

The temperature sensor circuit, Circuit 2, can be any well known circuit that responds to a change in voltage, current or resistance transmitted by the temperature sensor. In this embodiment, the temperature sensor circuit consists of a linear resistance input varying with temperature from the temperature sensor, National Semiconductor model number LM335AZ, connected to an analog to digital integrated circuit, National Semiconductor model number ADC0831CCN. The digital number representation of the temperature sensor is transmitted via wire to the microcontroller.

The motor driver circuit, Circuit 3, can be any well known motor driver circuit, such as Texas Instruments motor driver integrated circuit model number L293D. The motor driver transmits current to the arm motor and is capable of forward and reverse current polarity to move the arm mechanism horizontally back and forth. The motor driver is connected via wire to the microcontroller.

The microcontroller, controls the overall operation of all circuit components and mechanical parts. In the embodiment of the invention shown in FIG. 2A and FIG. 2B, the microcontroller used is a Parallax BS2-IC with the Microchip PIC16C57c and a Parallax protoboard. The microcontroller receives a digital signal from the temperature sensor circuit which represents the temperature of each metal block. The microcontroller is programmed with a predetermined hold temperature of each metal block. Until the temperature of each block reaches its hold temperature, the microcontroller maintains the current flow through Circuit 1 which drives each resistive heating element. Once each individual metal heating block reaches its respective hold temperature, the microcontroller stops current flow through Circuit 1. As the temperature of each heating block drops below the hold temperature, current flow through Circuit 1 is reactivated. The microcontroller effectively regulates and monitors the temperature of each heating block and maintains temperature uniformity of each heating block.

The microcontroller can be programmed to actuate the motor driver circuit, Circuit 2, at predetermined time intervals, directions and durations. This has the effect of activating the DC motor, thereby driving the arm gearing system. This translates into horizontal movement of the arm platform which shuttles the vessel between the slots of the metal heating blocks.

An example operation of the thermal cycling device consists of programming the microcontroller via keypad and display to hold an individual temperature of each heating block. The microcontroller is also programmed with a set number of cycles of arm movement. The microcontroller is also programmed with a set hold time of the vessel as it is moved into the slot of each heating block and as it is located between the two heating blocks.

A sample programmed run of the microcontroller could consist of (A) waiting for heating blocks to reach set temperatures, (B) movement of the vessel by the mechanical arm to the slot opening of the first block, (C) holding the cuvette at the first block for a set period of time, (D) movement of the vessel by the mechanical arm to the slot opening of the second block, (E) holdings the vessel at the second block for a set period of time, (F) repeating steps B to E for a set number of cycles, (G) moving the vessel to a location between the two heating blocks for removal.

The thermal cycling device component of the present invention, due to the constant temperature heating blocks, is capable of cycling reaction samples in a vessel through significantly shortened temperature versus time profiles compared to prior art. The device depicted FIGS. 1 and 2 can be used for a two-step DNA amplification reaction. The length of each reaction cycle is significantly reduced in comparison to that observed in standard, single-block thermal cyclers, since there is no temperature ramp-up and ramp-down of the temperature blocks required. The same reaction cycle using prior art devices would take approximately 5-10 times longer because of the ramping times. Decreased cycle times can lead to better yield and specificity of the polymerase chain reaction over prior art cycling. Specifically, in the past it has been found that ultra fast ramping times resulted in improved specificity and increased yields in PCR amplifications. Rapid cycling results in less time for primer extension at non-specific annealing sites, consequently, the amount of non-specific product is directly related to the time at the low temperature, which is the annealing temperature in standard PCR (Wittwer C. T. et al, Biotechniques, 10:76-83 (1991). A rapid cool-down (>5° C./sec) of the PCR mixture favors the kinetics of primer annealing over the thermodynamic advantage of product reannealing. This, in turn, results in an increased product yield.

Furthermore, a shortened time (for example, less than 5 seconds) required to bring the temperature of the reaction mixture from one temperature level to the next temperature level corresponding to phases in the amplification process, is facilitated in the system of the present invention. Specifically, the time is shortened in comparison to ramp times in standard PCR, especially standard PCR performed using a single-block device. The decrease in time required to change the temperature of the reaction, decreases the overall time required for to complete nucleic acid amplification.

The simplicity of the horizontal movement of the mechanical arm system between the two heating blocks, significantly decreases the complexity of control and cost of the thermal cycling device compared to those currently in use. Previous devices require complicated robotic arm construction and precise microprocessor control to achieve a similar movement of a reaction sample between heating blocks.

Amplification products obtained through the use of the thermal cycling device of the present invention are qualitatively and quantitatively similar to those obtained through the standard Peltier heating block cycling method. However, advantages in specificity and yield are possible with rapid thermal control of the reaction mixture using the device of the present invention. Such a rapid response is not possible with prior art systems.

By reducing the ramping time of the reaction sample, the present invention can markedly decrease the total time required for the polymerase chain reaction. In addition, the vessel can be designed to hold small reaction samples which reduces the amounts of expensive reagents which must be used thus further reducing the cost of carrying out procedures using the present invention.

The thermal cycling apparatus component of the present invention is useful for amplifying DNA from any source. Although particular configurations and arrangements of the present invention have been discussed in connection with the specific embodiments of the thermal cycling device as constructed in accordance with the teachings of the present invention, other arrangements and configurations may be utilized. For example, various cuvette or heating block configurations may alternatively be used in the thermal cycling device.

As will be appreciated by a worker skilled in the art, the thermal cycling device of the present invention provides even greater improvement over the prior art in the speed at which thermal cycling can be carried out, e.g., 30 cycles of DNA amplification in 10-30, or fewer, minutes. Furthermore, the thermal cycling apparatus provides better thermal homogenization throughout the samples than previously thought possible, without completely surrounding the reaction vessel by the temperature source.

It will be appreciated that the apparatus described herein can readily be used for many different applications including: polymerase chain reaction processes; cycle sequencing; and, other amplification protocols such as the ligase chain reaction. The present invention also advantageously provides an apparatus for accurately controlling the temperature of samples located in the reaction vessel and quickly and accurately varies the temperature of samples located in a vessel according to a predetermined temperature versus time profile.

The configuration of the thermal alternator device of the present invention allows it to be readily combined with detection systems, such as the fluorescence detection system described in more detail below. It should be readily appreciated, however, that the device is not limited to combination with a fluorescence detection system. For example, it can be easily adapted for use with systems, including but not limited to, a visible light detection system, a luminescence detection system or a magnetic detection or separation system. The configuration of the present device permits such adaptation to be well within the abilities of the skilled worker.

Technical Description of the Fluorescence Detection System

Figure 3:
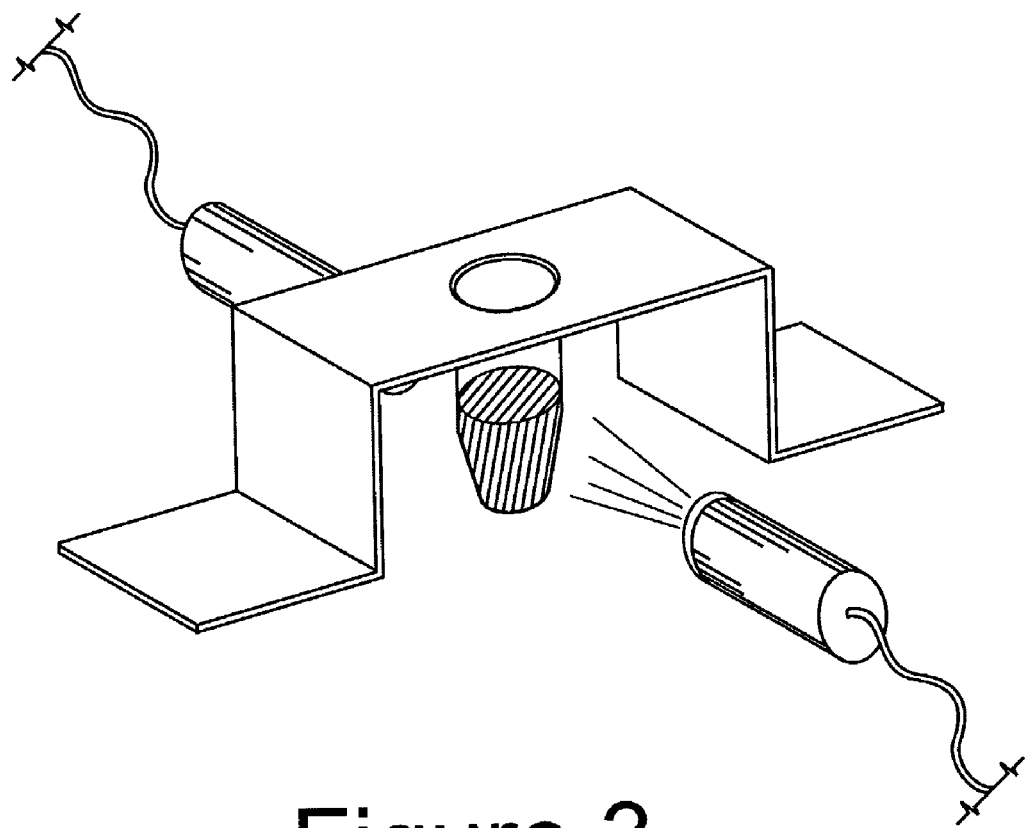
FIG. 3: is a perspective view of the fluorescence detection apparatus according to one embodiment of the present invention.

As shown in FIG. 3, the device of the present invention optionally includes a fluorescence detection system, which can be located directly between the two temperature heating blocks and beneath the horizontal translation means. The fluorescence detection system consists primarily of an excitation source and a detector for the emission source. The excitation source is a light source which will be described further below. The emission source is from the sample inside the cuvette. The sample fluoresces when illuminated by the excitation source. The detector consists of a photosensitive sensor, capable of quantifying the intensity of light produced by the emission source. As shown in FIG. 3, the excitation source and detector are located on opposite sides of the emission source, both of which will be described further below.

As shown in FIG. 3, the excitation source is located on one side of the vessel at an optimal distance to focus light into the chamber, thereby illuminating the sample. Preferably, the excitation source has a peak wavelength compatible with fluorescent dyes; for example 480 nm. In this embodiment, the excitation source is a blue Light Emitting Diode (LED) with a 3000 mcd at 30 mA and 15 degree focusing angle. The excitation source is enclosed within an opaque tube to prevent excess leakage of light from the source. The excitation light source wavelength is restricted with an optical low pass filter placed directly in the path of light. An optical filter is needed to differentiate the emission from excitation wavelength. In this embodiment, a 500 nm low pass blue dichronic filter is placed in the path of light from the excitation source.

As shown in FIG. 3, the emission source is located within the vessel. The emission source consists of a fluorescent entity and a nucleic acid amplification product. When illuminated by the excitation source, the entity (for example, a double-stranded DNA specific dye or a fluorescently labeled probe) and nucleic acid amplification product emits light at a different peak wavelength than the excitation source. Examples of suitable fluorescent dyes include, but are not limited to, thiazole orange, SYBR™ GREEN I, ethidium bromide, pico green, acridine orange, YO-PRO-1, and chromomycin A3. Alternatively the fluorescent entity is a nucleic acid probe that is specific for the amplification product and that is labeled with a fluorescent tag.

As shown in FIG. 3, the detector is located on one side of the vessel, directly opposite the excitation source, at an optimal distance to collect light from the emission source. Preferably, the detector is a photosensitive sensor capable of differentiation of visible light at a chosen peak wavelength. In this embodiment, the detector consists of a CDS photodiode. The detector is enclosed within an opaque tube to prevent excess light from being detected by the sensor. The wavelength of light detected by the sensor is restricted with an optical filter placed direction in the path of the emission source. An optical filter is needed to differentiate the emission source from the excitation wavelength. In this embodiment, a 520 nm band pass green dichronic filter is placed in the path of light from the emission source.

Both the excitation source and the detector are activated by means of the microcontroller. In this embodiment, when a fluorescence reading of the sample within the vessel is desired, the microcontroller activates the excitation source. The excitation source then illuminates the emission source. The light generated by the emission source strikes the detector. In this embodiment, a relative amount of light from the emission translates into a change in resistance of the photodiode detector. This resistance is monitored via wire by the microcontroller. Any change in fluorescence translates into a change detected by the microcontroller.

In a sample run of the fluorescence detection system, a sample within a reaction vessel is placed into the thermal cycling device. A fluorescence measurement is taken at the ambient temperature of the device. Following this measurement, the PCR reaction takes place over a predetermined number of cycles. Following the completion of the PCR reaction, the vessel is positioned between the fluorescence detection system and another measurement is taken. By comparing the initial and final fluorescence of the sample in the vessel, a corresponding increase in nucleic acid amplification product can be determined. Fluorescence measurements may also be taken at the completion of each PCR cycle, thereby quantifying per cycle the relative amount of nucleic acid amplification product increase.

The fluorescence detection component of the present invention, due to the simplicity of design, is capable of measuring per cycle results of nucleic acid amplification product by means of fluorescence. Compared to prior art fluorescence detection systems implemented in heating block thermal cyclers, this device component offers significant reduction in mechanical complexity and cost, while maintaining similar performance capabilities. DNA amplification can be measured by means of fluorescence at the beginning and end of the PCR reaction, as well as during each step. This same performance measurement using prior art system would be approximately 100 times more expensive. The simplistic optics, excitation source and detector of the present invention, have proven also to produce comparable results to more expensive and complex prior art systems.

Furthermore, the rapid cycling of the thermal cycling component means a quantitative fluorescence measurement of nucleic acid product can be accomplished much faster than prior art systems. This greatly reduces the time required to quantify any nucleic acid product generated by the PCR reaction.

Also, the simplicity of design of the detection system, significantly decrease the complexity of control, result generation and cost compared to prior art systems. A prior art device requires expensive optics to focus and split the excitation and emission source, as well as a sensor and computer to process and interpret the results. In prior art systems, this is usually done by means of a CCD sensor image which is analyzed by image processing algorithms by a computer.

Figure 5:
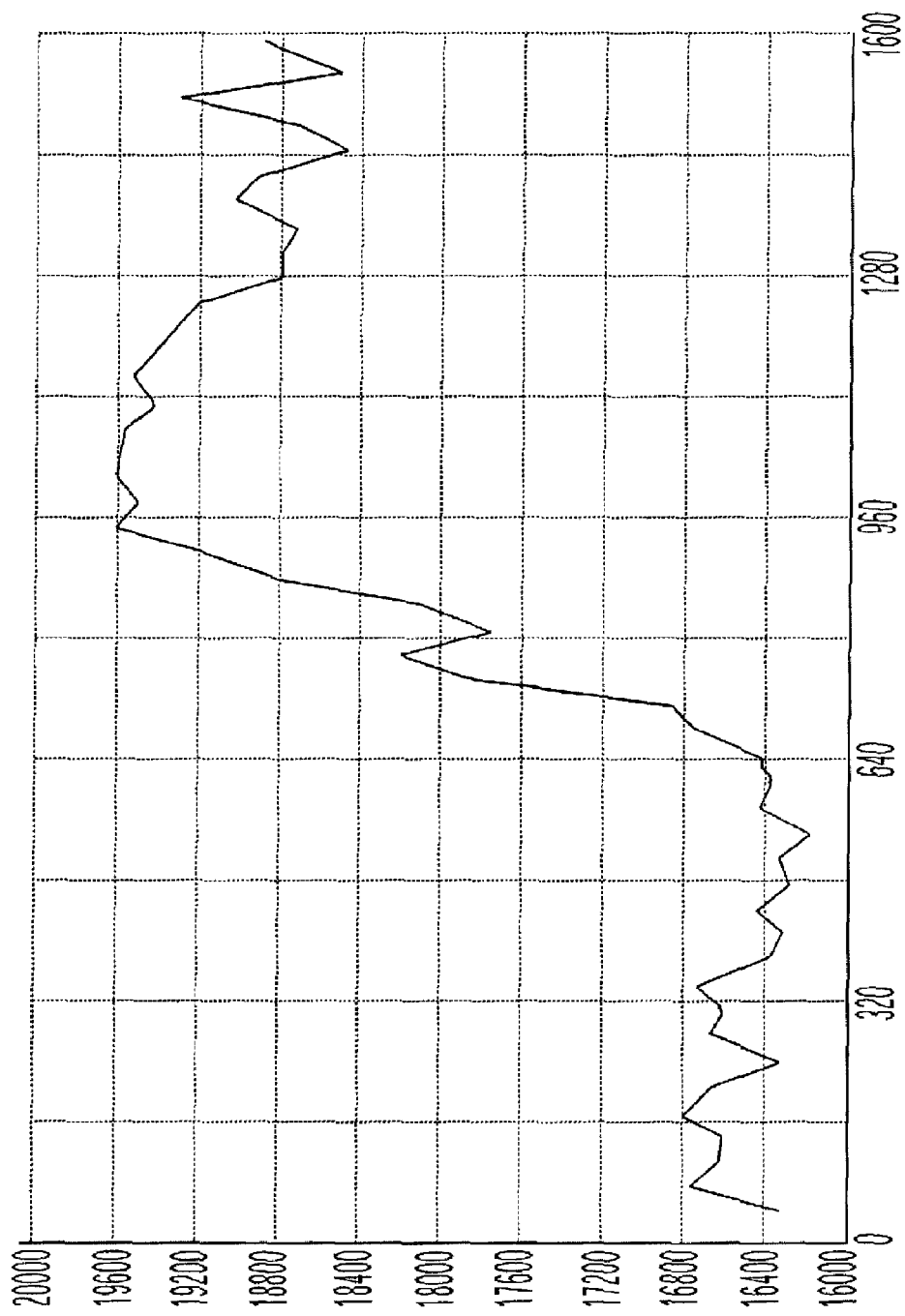
FIG. 5: is an optical/graphical read-out from a singleplex PCR performed in a thermal alternator according to one embodiment of the present invention using detection apparatus.

Fluorescence detection measurements obtained through the use of the fluorescence detection device in the present invention are qualitatively and quantitatively similar to those obtained through similar prior art systems. However, the measurements yielded can be achieved much faster and using a simpler design. FIG. 5 shows the fluorescence intensity versus time of the fluorescence detection device used in conjunction with the thermal cycling device. The steady increase in fluorescence corresponds to an increase in nucleic acid amplification product. As can be seen, fluorescence is quantifiable on a per cycle basis. Such measurement performance can only be duplicated with prior art systems at a significant complexity and cost increase.

As has been shown, by implementing a simplified design for fluorescence detection measurement, the present invention can markedly decrease the device complexity and cost, while maintaining similar performance characteristics of prior art systems. In addition, the per cycle measurement capability allows fewer PCR cycles to be performed on the reaction sample before a positive indication of nucleic acid amplification product is produced. This translates into reduced time needed to identify a positive reaction.

The fluorescence detection measurement system is useful for detecting the presence of fluorescence within a vessel from any source. Although particular configurations and arrangements of the present invention have been discussed in connection with the specific embodiments of the fluorescence detection device in accordance with the teachings of the present invention, other arrangements and configurations may be utilized. For example the emission source may alternatively be located at the top of the reaction vessel, and the detector at the bottom of the vessel.

The fluorescence detection device provides even greater reduction in complexity and cost over the prior art systems. Furthermore, the fluorescence detection device provides comparable per cycle measurements when compared to prior art systems.

EXAMPLES

Example 1

Singleplex Real-Time PCR Using a 2-Temperature Cycle on the Thermal Cycling Device Methods and Material The polymerase chain reaction was run in a 50 µl volume with ~50 ng template DNA (methicillin-resistance *Staphylococcus aureus*), 0.125 mM of each deoxynucleotide, 0.25 µM of each oligonucleotide primer (Forward Primer: Mec-1F, gtcgtaactatcctctagaaaaagcgacttc; Reverse Primer: Mec-1R, tgacacgatagccatcttcatgttg) in a reaction buffer consisting of 50 mM KCl, 10 mM Tris-HCl, pH 8.3, 2.5 mM magnesium chloride. In addition, 5 µl of Sybr™ Green dye (10,000× stock diluted 1:1000) was added to the reaction. *Thermus aquaticus* polymerase (7.5 units of Taq Polymerase, Invitrogen) was added, the samples placed in a typical 0.2 ml thin-walled PCR tube (GeneAmp, Applied Biosystems). Since the lid in this model of the thermal cycling device is not heated, mineral oil (one drop) was overlaid on top of the reaction fluid to prevent evaporation.

The PCR tubes were then placed in the thermal cycling device or an Applied Biosystem GenAmp 2700™. In the device, the tubes were placed vertically in the holder which is constructed of a horizontally moving arm on geared-tracks (adapted from a CD-ROM drive). In both the device and the ABI 2700, the mixture was cycled 45 times through denaturation (95° C.) and annealing/extension (60° C.). An initial denaturation step was done for 15 seconds. During each cycle, the denaturation step lasted 10 seconds and the annealing/extension step was 20 seconds. Temperature monitoring of the tubes was done with an internal monitor that was embedded in the copper block. Amplification products were fractionated by electrophoresis on a 1.5% agarose gel.

Results

Figure 4:
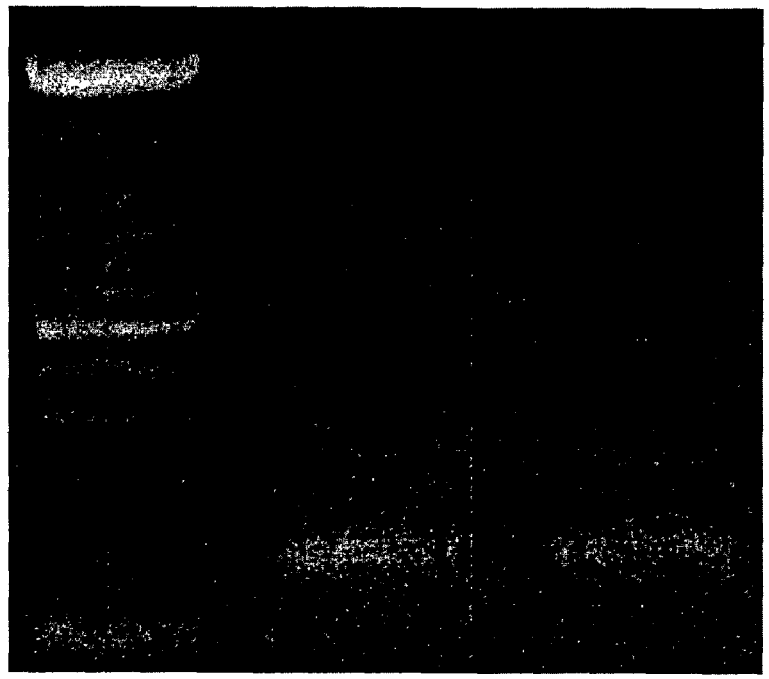
FIG. 4: is a photograph of an agarose gel separation of singleplex PCR products obtained from reactions performed in a thermal alternator according to one embodiment of the present invention and in an ABI GeneAmp® 2700.

FIG. 4 shows the agarose gel electrophoresis of the reaction contents. The 180 b.p. amplicon is seen for both the thermal cycling device and the ABI 2700. While the thermal cycling device cycled through the complete reaction in approximately 25 minutes, it took greater than 80 minutes for the ABI 2700 to complete the cycling profile.

FIG. 5 illustrates a graphical readout in real-time of the reaction on the thermal cycling device.

Figure 6:
FIG. 6: is a photograph of reaction tubes under UV light, wherein the reaction tubes contain mixtures from singleplex PCRs performed in a thermal alternator according to one embodiment of the present invention.

FIG. 6 shows a negative control reaction vessel (left) and a positive control reaction that was run on the thermal cycling device (right). The tubes were visualized, in this instance, on a UV lamp. It is apparent that the reaction has an increased density in the positive sample.

Example 2

Multiplex PCR (3plex) Using a 2-Temperature Cycle on the Thermal Cycling Device

Methods and Materials

The polymerase chain reaction was run in a 30 µl volume with ~50 ng template DNA, 0.25 mM of each deoxynucleotide 0.02 µM of each oligonucleotide primer in a reaction buffer consisting of 50 mM KCl, 10 mM Tris-HCl (pH 8.5), 7.5 mM magnesium chloride. *Thermus aquaticus* polymerase (2.5 units of Taq polymerase, Invitrogen) was added, the samples placed in a typical 0.2 ml thin-walled PCR tube (GeneAmp, Applied Biosystems). Since the lid in this model of the thermal cycling device is not heated, mineral oil (one drop) was overlaid on top of the reaction fluid to prevent evaporation.

The PCR tubes were then placed either in the thermal cycling device or an ABI 2700. The mixture was cycled 45 times through denaturation (95° C.) and annealing/extension (60° C.). An initial denaturation step was done for 15 seconds. During each cycle, the denaturation step lasted 10 seconds and the annealing/extension step was 20 seconds. Temperature monitoring of the tubes was done with an internal monitor that was embedded in the copper block. Amplification products were fractionated by electrophoresis on a 1.5% agarose gel.

Primers:

| MRSA Gene | Primer Name | Sequence (5' to 3') | Size |
|---|---|---|---|
| NUC | NUC-F | aaagggcaatacgcaaagaggttt | 598 bp |
|  | NUC-R | gacctgaatcagcgttgtcttcg |  |
| MecA | MecA-F | tgagattaggcatcgttccaaagaa | 392 bp |
|  | MecA-R | tgacacgatagccatcttcatgttg |  |
| 16S rRNA | 16s rRNA-F | actcgactacatgaagctggaatcg | 312 bp |
|  | 16s rRNA-R | ccttccgatacggctaccttgttac |  |

Results

Figure 7:
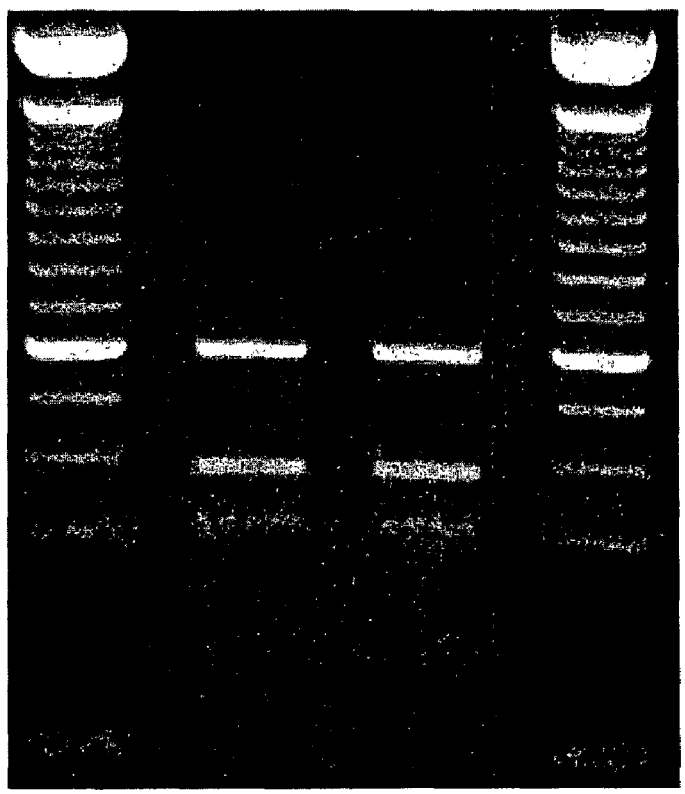
FIG. 7: is a photograph of an agarose gel separation of multiplex PCR products obtained from reactions performed in a thermal alternator according to one embodiment of the present invention and in an ABI GeneAmp® 2700.

A two-temperature multiplex PCR was performed in which the annealing and extension steps were performed at a single temperature. FIG. 7 shows the gel electrophoresis results. Equivalent 3plex results were seen on the thermal cycling device and the ABI 2700.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A device for thermal cycling of a reaction mixture contained within a reaction vessel, said vessel including a side wall, said device comprising:
(a) at least two heating blocks in spaced apart generally opposing relation, each of said blocks including a substantially vertical wall, said walls each including at least one generally vertical groove recessed therein open towards the opposing grooved wall of said blocks to receive said at least one vessel such that said vessel may be placed into said groove with said groove only partly surrounding said sidewall with the remainder of said sidewall being exposed to ambient conditions;
(b) a holder for holding said reaction vessel between said blocks, said holder for retaining said vessel such that when engaged within one of said grooves the exposed portion of said sidewall is exposed to ambient conditions;
(c) means for maintaining said at least two heating blocks at set temperatures different from each other, for carrying out a thermal cycling chemical reaction;
(d) drive means for imparting relative motion between said vessel and said blocks such that generally opposing sides of said vessel sequentially contact said heating blocks, such that said vessel is partially enclosed within a selected one of said grooves when in contact with each said block, and laterally displaceable between said grooves, wherein said motion comprises a linear and unidirectional horizontal path followed by said vessel relative to said blocks.

2. The device of claim 1 wherein said holder retains said vessel such that said vessel depends downwardly from said holder and the sidewall of said reaction vessel is substantially fully exposed when held by said holder.

3. The device of claim 1, wherein said at least two heating blocks each include a plurality of said grooves in spaced parallel relation to each other, and said sample holder includes means for holding a plurality of said reaction vessels.

4. The device of claim 1, wherein said holder includes at least one opening extending horizontally therethrough for suspending said at least one vessel with substantially all of its sidewall exposed, and said drive means is for displacing said holder along a path between said blocks.

5. The device of claim 1, comprising only two heating blocks in spaced opposing relation to each other, wherein said grooves directly oppose each other.

6. The device of claim 1, further comprising temperature sensing means for sensing the temperature within said reaction vessels, and temperature control means for increasing or decreasing the temperature of at least one of said blocks in response to the temperature sensed by said sensing means.

7. The device of claim 6, wherein said temperature sensing means comprises thermostat wiring in each heating block, each wiring being at least partially positioned within the heating block and sufficiently close to said groove to detect temperature of said reaction vessel.

8. The device of claim 1, wherein said grooves are dimensioned to contact between about 40% and 50% of the side wall of said reaction vessel.

9. The device of claim 1, wherein said blocks are stationary and said drive means is for moving said reaction vessels in a linear motion between said blocks.

10. The device of claim 1, further comprising a controller for controlling operation of the device.

11. The device of claim 1, wherein said drive means comprises an arm extending between said blocks, said arm including openings for releasably holding said reaction vessels wherein said vessels depend from said arm, said arm having a sleeve, a rotatable shaft, a threaded shaft, and means for rotatably driving said shaft, said arm including a sleeve having means to engage the threading of said shaft wherein rotation of said shaft causes displacement of said arm along said shaft, and means to selectively reverse direction of rotation of said shaft, wherein rotation in a first direction causes linear movement of said arm towards a first of said block, and rotation of such shaft in a second direction causes linear movement of said arm towards a second of said blocks.

12. The device of claim 1, further comprising monitoring means for monitoring of nucleic acid amplification product formation within said at least one reaction vessel, said reaction vessel having a translucent side wall, said monitoring means comprising:

at least one visible light source for illuminating a volume of the mixture;

at least one first optical filter for restricting the wavelength of light entering the mixture from the light source;

at least one second optical filter for restricting the wavelength of a fluorescent signal emitted from the mixture; and a detection and analysis means for receiving the fluorescent signal at any time point before, during, or after a nucleic acid amplification, the detection and analysis means measuring the intensities of the fluorescent signal at a predetermined time point, producing a plurality of corrected intensity signals, each corrected intensity signal corresponding to a relationship between the intensities of the fluorescent signal at a predetermined time point and before the nucleic acid amplification.

13. The device of claim 12, wherein the detection and analysis means provides a readout corresponding to the plurality of corrected intensity signals as a function of time.

14. The device of claim 12, wherein the reaction vessel includes an optical interface through which light from the light source is transmittable into the mixture.

15. The device of claim 14, wherein the optical interface forms a wall of the reaction vessel that covers at least a portion of the mixture and which is separated from the sample by an air gap.

16. The device of claim 1 further comprising at least one reaction vessel comprising a plastic microtube.

17. The device according to claim 12 wherein said at least one reaction vessel comprises a plurality of reaction vessels, said at least one light source comprises a plurality of light sources and said at least one first and second optical filters comprise a plurality of first and second optical filters, and further comprising a multiplexer that couples the detection and analysis means to the light sources.

* * * * *